United States Patent
Brodbeck et al.

(10) Patent No.: US 8,992,526 B2
(45) Date of Patent: Mar. 31, 2015

(54) SURGICAL INSTRUMENT

(75) Inventors: Achim Brodbeck, Metzingen (DE); Dieter Hafner, Offenburg (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 1337 days.

(21) Appl. No.: 11/573,958

(22) PCT Filed: Jul. 12, 2005

(86) PCT No.: PCT/EP2005/007559
§ 371 (c)(1), (2), (4) Date: Feb. 20, 2007

(87) PCT Pub. No.: WO2006/021269
PCT Pub. Date: Mar. 2, 2006

(65) Prior Publication Data
US 2009/0043305 A1 Feb. 12, 2009

(30) Foreign Application Priority Data
Aug. 24, 2004 (DE) .......................... 10 2004 040 959

(51) Int. Cl.
*A61B 18/14* (2006.01)

(52) U.S. Cl.
CPC ..... *A61B 18/1445* (2013.01); *A61B 2018/1412* (2013.01); *A61B 2018/1455* (2013.01)
USPC .................. 606/51; 606/46; 606/52; 606/207

(58) Field of Classification Search
CPC ............................................. A61B 2018/1455
USPC ................................ 606/46, 50–52, 205–211
See application file for complete search history.

(56) References Cited

U.S. PATENT DOCUMENTS

| 5,334,198 | A | * | 8/1994 | Hart et al. | ........................ 606/52 |
| 5,445,638 | A | | 8/1995 | Rydell et al. | |
| 5,458,598 | A | | 10/1995 | Feinberg et al. | |
| 5,569,299 | A | * | 10/1996 | Dill et al. | ........................ 606/205 |
| 5,700,276 | A | * | 12/1997 | Benecke | ........................ 606/208 |
| 5,797,938 | A | * | 8/1998 | Paraschac et al. | ............ 606/167 |
| 5,797,941 | A | | 8/1998 | Schulze et al. | |
| 5,800,449 | A | | 9/1998 | Wales | |
| H1904 | H | * | 10/2000 | Yates et al. | ........................ 606/50 |
| H2037 | H | * | 7/2002 | Yates et al. | ........................ 606/51 |
| 6,558,385 | B1 | | 5/2003 | McClurken et al. | |
| 2002/0099371 | A1 | | 7/2002 | Schulze et al. | |
| 2002/0188294 | A1 | * | 12/2002 | Couture et al. | ................. 606/51 |
| 2003/0125728 | A1 | | 7/2003 | Nezhat et al. | |
| 2004/0116924 | A1 | | 6/2004 | Dycus et al. | |

(Continued)

FOREIGN PATENT DOCUMENTS

DE 44 21 822 C1 10/1995
EP 0 724 863 A2 8/1996

(Continued)

*Primary Examiner* — Jaymi Della
(74) *Attorney, Agent, or Firm* — Dickstein Shapiro LLP

(57) ABSTRACT

Surgical instruments are provided for performing laparoscopic or similar minimally invasive operations, including two clamping parts, which can move towards one another and which have clamping surfaces for gripping tissue when they are closed. A cutting device has a cutting edge that, in a cutting direction, can be displaced relative to the clamping parts for cutting the gripped tissue. In such an instrument the cutting direction extends at an acute angle to the clamping surfaces when they are closed.

7 Claims, 3 Drawing Sheets

(56) References Cited

U.S. PATENT DOCUMENTS

2005/0131402 A1* 6/2005 Ciarrocca et al. ............... 606/41
2006/0079891 A1* 4/2006 Arts et al. ....................... 606/51

FOREIGN PATENT DOCUMENTS

| JP | 2005-144193 A | 6/2005 |
| WO | 95/18573 A1 | 7/1995 |

* cited by examiner

SURGICAL INSTRUMENT

CROSS-REFERENCE TO RELATED APPLICATIONS

This application is a Section 371 of International Application No. PCT/EP2005/007559, filed on Jul. 12, 2005, which was published in the German language on Mar. 2, 2006, under International Publication No. WO 2006/021269 A1 and the disclosure of which is incorporated herein by reference. International Application No. PCT/EP2005/007559 claims priority to German Patent Application No. 10 2004 040959.5, filed Aug. 24, 2004.

BACKGROUND OF THE INVENTION

The invention concerns a surgical instrument with at least two clamping parts and a cutting device for use, in particular, in laparoscopic or similar minimally invasive operations.

Instruments of this type are used to cut, prepare and coagulate tissue, in particular in minimally invasive surgery, e.g. laparoscopy. A requirement of instruments of this type is that tissue can be safely gripped in a simple manner and then be cut through equally safely. At the same time, it is also important that there is no risk of damaging the surrounding tissue as a result of cutting through the tissue and the cutting movement this requires.

An instrument of this type, which is configured as a tubular shaft instrument and has electrodes in order to coagulate the gripped tissue, is known from U.S. Pat. No. 5,445,638.

The problems with this instrument are considered to be that, on the one hand, there is considerable wear to the cutting instrument while, on the other, the tissue slips relatively easily from the clamping surfaces when being cut through and thus is not cut through completely.

BRIEF SUMMARY OF THE INVENTION

The object of the invention is to provide a surgical instrument of the type specified initially that combines an improved cutting action with good and safe operability.

According to the invention there is provided a surgical instrument, in particular for laparoscopic or similar minimally invasive operations, comprising at least two clamping parts, which can be moved towards each other and which have clamping surfaces for gripping tissue when they are closed, and a cutting device with a cutting edge, which can be moved in a cutting direction relative to the clamping parts to cut gripped tissue, the cutting device extending at an acute angle relative to the clamping surfaces when they are closed.

In the present invention the clamping surfaces do not hold the tissue—as in the state of the art instruments initially specified—in such a way that the cutting device only exerts forces on the tissue in directions that tend to move the gripped tissue out of the grip of the clamping surfaces. Rather, the angular arrangement ensures that at least parts of the cutting force exerted acts in a direction perpendicular to the clamping surfaces and thus the tissue tends to remain securely in the grip of the clamping surfaces. At the same time, good operability of the instrument is achieved since the instrument can be arranged in such a way that, with opened clamping parts, an advance motion for the grasping of tissue occurs substantially in the direction of an angle bisector between the clamping surfaces, which is of great advantage with laparoscopic operations in particular.

A further advantage of the instrument according to the invention is that the cutting edge of the cutting device on its path through the opening between the clamping surfaces does not continually meet the same section of the tissue, but rather the cut tissue travels over the cutting edge, with the result that, on the one hand, it is cut rather than pressed and, on the other, the cutting edge is used over a larger longitudinal section and thus is worn less.

The cutting device may be configured as a HF surgical cutting device or, however, as a mechanical cutting device (like a scalpel).

Preferably, the cutting edge is inclined at an obtuse angle relative to the cutting direction, which improves the actual cutting action. In addition, the path over which the cutting device must be moved is reduced. This angle of inclination may be constant over the length of the cutting edge relative to the cutting direction or alter with a cutting edge curved like an arc over the latter's length. With such a cutting edge that is curved like an arc, a "soft" first cut may be made, which then becomes a steeper, more forcefully cutting progression of cut.

Preferably, one of the clamping parts is immovable relative to the cutting direction. As a result, the operator will have a fixed reference point when grasping tissue. In addition, the mechanics for moving the clamping parts are simple.

Preferably, the surgical instrument is attached at one distal end of a mount to form a tubular shaft instrument for laparoscopic or similar minimally invasive operations. The instrument thus configured handles well. In particular, tissue is easy to grasp and prepare due to the inclination with respect to an axis of the tubular shaft.

The clamping surface will preferably have, in an essentially conventional manner, electrodes for supplying a HF coagulating current to the tissue, so that tissue grasped by the clamping surfaces can be coagulated and then cut through.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
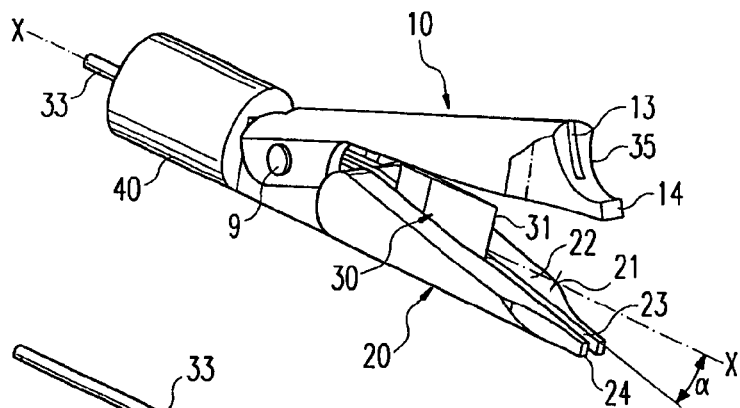
FIG. 1 is a perspective view of a first embodiment of the invention.
Figure 3:
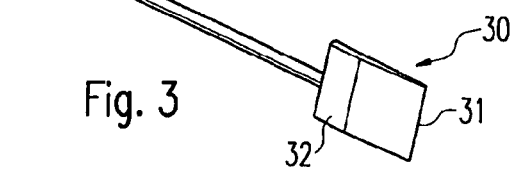
FIG. 3 is a perspective view of a cutting device.
Figure 2:
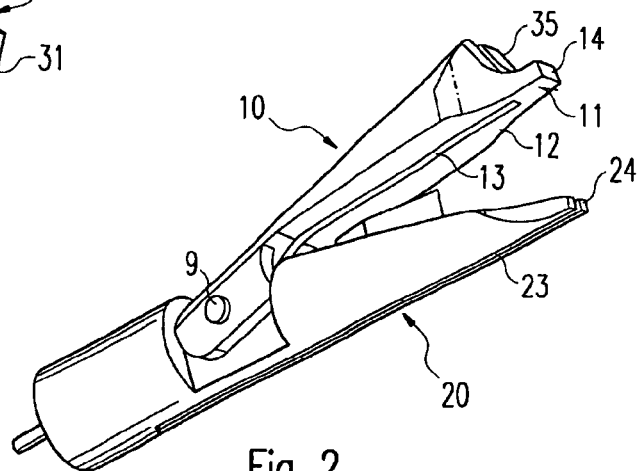
FIG. 2 is a perspective view of the embodiment shown in FIG. 1 from another angle.
Figure 4:
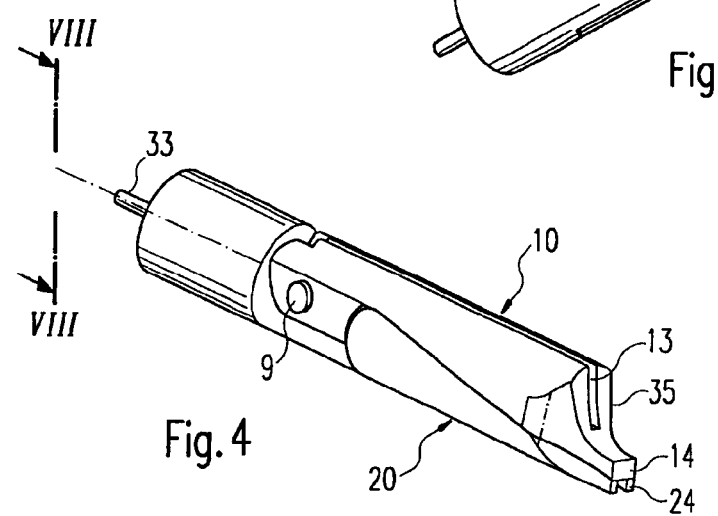
FIG. 4 is a perspective view of the embodiment shown in FIG. 1 with its clamping parts closed.
Figure 5:
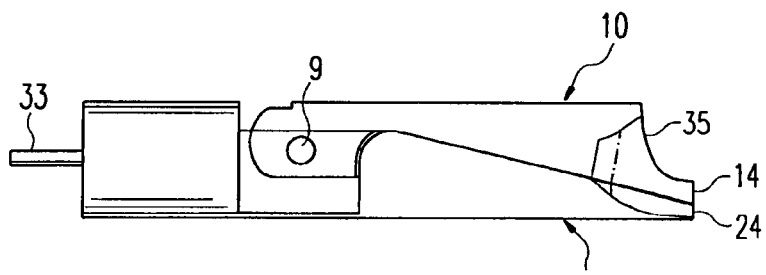
FIG. 5 is a side elevation of the embodiment shown in FIG. 4.
Figure 6:
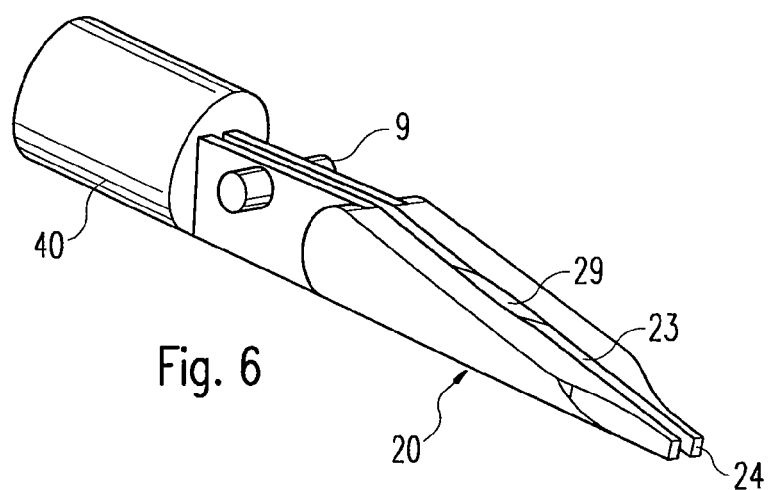
FIG. 6 is a perspective view of the embodiment shown in FIG. 2 but with one clamping part removed.
Figure 7:
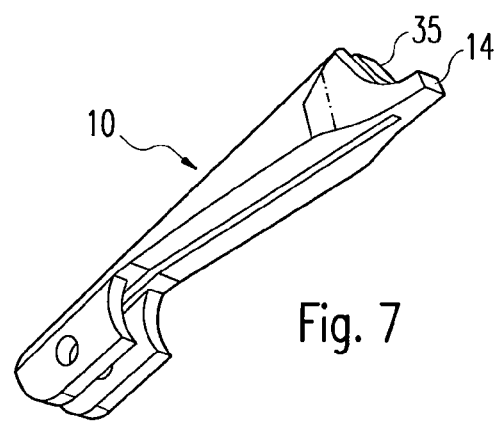
FIG. 7 is a perspective view of the removed clamping part for attachment to the instrument shown in FIG. 6.
Figure 8:
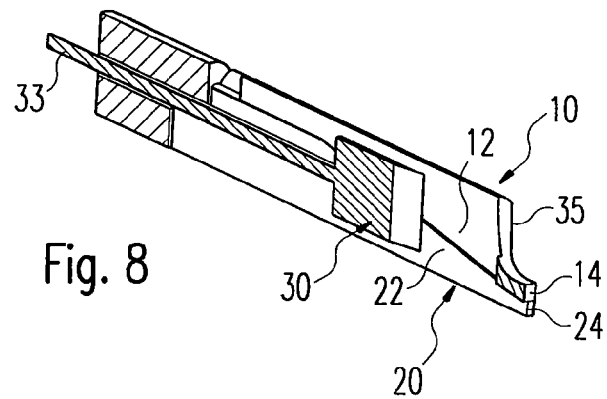
FIG. 8 is a cross-section along the line VIII-VIII in FIG. 4.

In the following description, the same reference numerals are used for the same and similarly working parts.

As shown in FIGS. 1-8, the surgical instrument comprises a first, in the drawings upper, clamping part 10 and a second, in the drawings lower, clamping part 20. Each of the clamping parts 10 and 20 has a clamping surface 11 and 21 respectively, which are fitted in an essentially conventional way with electrodes 12 and 22 respectively. The clamping parts 10 and 20 are connected to each other via an articulated joint 9, wherein the (upper) clamping part 10 has an actuating device, which is familiar in itself and, for the sake of simplicity, has not been depicted in the figures.

When tissue is clamped between the two clamping surfaces 11 and 21, a HF current may be passed via the electrodes 12, 22 into the tissue for coagulating the same.

The upper clamping part 10 and the lower clamping part 20 each have a groove 13 and 23 respectively, in which a cutting device 30 with a cutting surface 32 and a front cutting edge 31 can be moved backwards and forwards via a push rod 33. The clamping surfaces 11, 21 have in the closed state (FIG. 4/5) an angle $\alpha$ (see FIGS. 1, 9) with respect to a longitudinal axis X, in which the cutting device 30 can be moved backwards and forwards via its push rod 33. This acute angle corresponds essentially in the embodiment depicted in FIG. 1-8 to the angle bisector between the two clamping surfaces 11, 21 in their opened state (FIG. 1). The lower clamping part 20 is rigidly attached to a mount 40, which forms part of a tubular shaft instrument, as is generally familiar. As a result of the arrangement thus made, it is possible to move the tubular shaft instrument in its direction of movement along the axis X towards a tissue that is to be gripped and to grasp the same. This direction of movement is particularly favourable for the person operating.

The point 14 of the upper clamping part and the point 24 of the lower clamping part are each configured to be streamlined, allowing even small sections of tissue to be gripped securely.

In the embodiment of the invention depicted in FIGS. 1-8 the cutting device 30 with its cutting edge 31 emerges from the groove 13 of the upper clamping part 10 when the cutting edge 31 has arrived at its foremost (distal) position.

Figure 9:
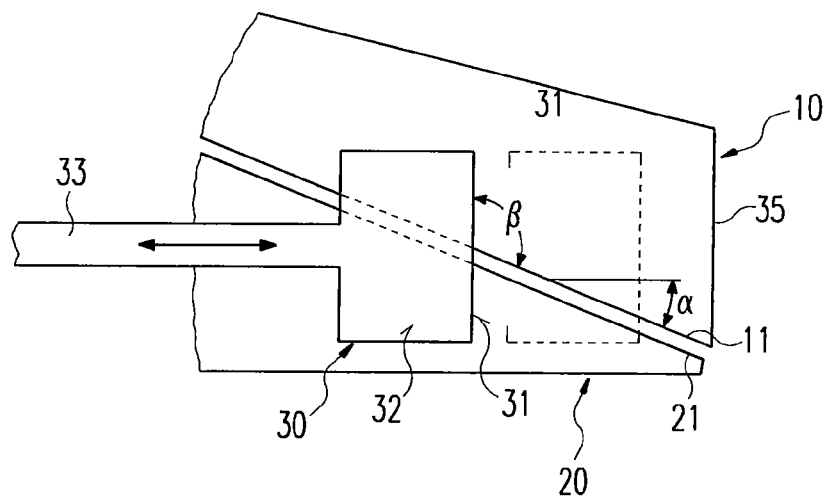
FIG. 9 is a schematic sectional view showing the angular arrangement of the clamping parts and cutting device.

To achieve protection here against damage to the surrounding tissue, a front edge 35 of the upper clamping part 10 projects so far forward in the embodiment shown in FIG. 9 that the cutting edge 31 is completely protected at the extreme front position of the cutting device 30.

Figure 10:
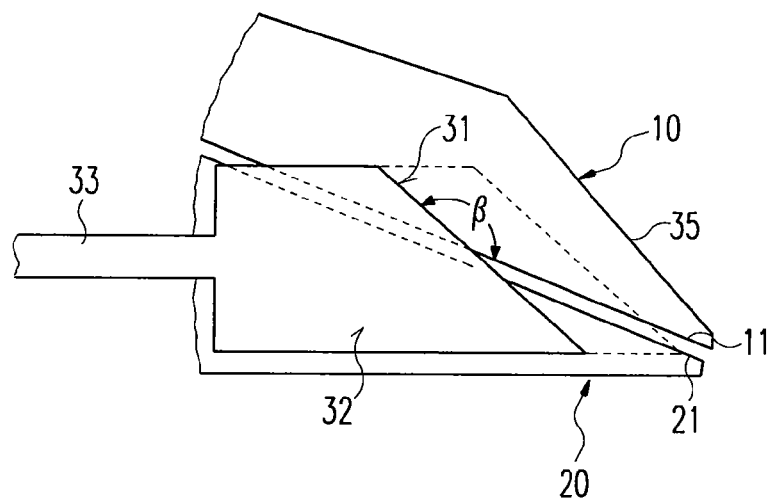
FIG. 10 is a view similar to FIG. 9 but of a first modified arrangement with an inclined cutting edge.

In the embodiment shown in FIG. 10, the obtuse angle A, at which the cutting edge 31 is inclined relative to the clamping surfaces 11, 21 (in the closed state), is larger than in the embodiment shown in FIG. 9. As can be seen from comparing FIGS. 9 and 10, the path on which the cutting device 30 must be moved along the axis X to travel from the central position depicted in the figures to the foremost position is smaller than in the embodiment shown in FIG. 9 (reference is made to the dashed line). In addition, the front edge 35 may be chamfered, without the cutting edge 31 in the foremost position of the cutting device 30 emerging from the instrument. The result is a more streamlined configuration.

Figure 11:
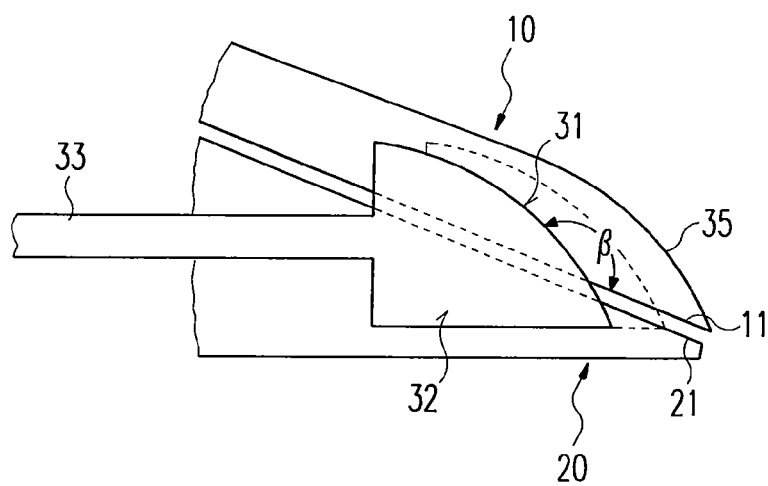
FIG. 11 is a view similar to that shown in FIG. 9 but of a second modified arrangement with an arcuate cutting edge.

The embodiment of the invention depicted in FIG. 11 differs from the one shown in FIG. 10 in that the cutting edge 31 is not constructed to be evenly inclined but rather arched. As a result, the upper clamping part 10 may be configured to be even more streamlined, on the one hand, while, on the other, a "softer" first cut is achieved when the cutting device 32 is displaced from its retracted position (the position shown on the left in the figures) into its advanced position and thus the angle between a section of clamped tissue is at first level, almost parallel to the clamping surfaces 11, 21, and then varies in relation to these, becoming increasingly steeper.

In addition, it is also possible to configure the clamping surfaces 11, 21 not only rectilinearly but also curving, which is particularly advantageous for many preparation purposes.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A surgical instrument, comprising:
   first and second clamping parts, which each have a clamping surface for gripping tissue, a tip at a respective first end of the first and second clamping parts and a respective joint portion at a second end of the first and second clamping parts, wherein the first and second clamping parts can be brought into a closed state in which the clamping surfaces contact each other, and wherein the clamping surfaces define in the closed state a closed state plane that extends directly from the joint portions of the first and second clamping parts directly to the tips of the first and second clamping parts; and
   a cutting device with a cutting edge, which can move in a cutting direction relative to the first and second clamping parts to cut the gripped tissue, wherein the cutting edge can be moved in a direction that is parallel to a longitudinal axis of the surgical instrument, and
   wherein the surgical instrument is configured such that the closed state plane is inclined at an acute angle relative to the cutting direction.

2. The surgical instrument according to claim 1, wherein said cutting edge is inclined at an obtuse angle relative to the cutting direction.

3. The surgical instrument according to claim 1, wherein said cutting edge has an arced configuration.

4. The surgical instrument according to claim 1, wherein one of said first and second clamping parts is fixed relative to the cutting direction.

5. The surgical instrument according to claim 1, wherein the surgical instrument is further adapted to be attached at a distal end of a mount so as to form a tubular shaft instrument for use in minimally invasive operations.

6. The surgical instrument according to claim 1, wherein said first and second clamping surfaces comprise electrodes adapted to supply a high frequency (HF) coagulating current to the tissue.

7. The surgical instrument according to claim 1, wherein the cutting edge is inclined towards the clamping surfaces in the closed state.

* * * * *